(12) United States Patent
Perkins et al.

(10) Patent No.: US 10,358,714 B2
(45) Date of Patent: Jul. 23, 2019

(54) SYSTEM AND METHOD FOR DEPOSITION OF INTEGRATED COMPUTATIONAL ELEMENTS (ICE) USING A TRANSLATION STAGE

(71) Applicant: Halliburton Energy Services, Inc., Houston, TX (US)

(72) Inventors: David L. Perkins, Easton, PA (US); Robert Paul Freese, Pittsboro, NC (US); Christopher Michael Jones, Houston, TX (US); Richard Neal Gardner, Raleigh, NC (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/309,432

(22) PCT Filed: Jun. 30, 2014

(86) PCT No.: PCT/US2014/044817
§ 371 (c)(1),
(2) Date: Nov. 7, 2016

(87) PCT Pub. No.: WO2016/003400
PCT Pub. Date: Jan. 7, 2016

(65) Prior Publication Data
US 2017/0175256 A1 Jun. 22, 2017

(51) Int. Cl.
*C23C 14/22* (2006.01)
*C23C 14/24* (2006.01)
(Continued)

(52) U.S. Cl.
CPC ............ *C23C 14/547* (2013.01); *C23C 14/22* (2013.01); *C23C 14/221* (2013.01); *C23C 14/24* (2013.01);
(Continued)

(58) Field of Classification Search
CPC ....... C23C 14/54; C23C 14/30; C23C 14/505; C23C 14/26; C23C 14/221; C23C 14/547;
(Continued)

(56) References Cited

U.S. PATENT DOCUMENTS

| 5,454,919 A | 10/1995 | Hill et al. |
| 6,148,239 A | 11/2000 | Funk et al. |

(Continued)

FOREIGN PATENT DOCUMENTS

| EP | 1182271 | 2/2002 |
| WO | 9313240 | 7/1993 |

(Continued)

OTHER PUBLICATIONS

International Search Report and Written Opinion of PCT Application No. PCT/US2014/044817 dated Mar. 3, 2015: pp. 1-14.

*Primary Examiner* — Kelly M Gambetta
(74) *Attorney, Agent, or Firm* — Chamberlain Hrdlicka

(57) ABSTRACT

The disclosed embodiments include a system and method for manufacturing an integrated computational element (ICE) core. In one embodiment, the method comprises thermally evaporating a material to deposit the material on a substrate, wherein the material is deposited to establish a shape of the ICE core. The shape of the ICE core defines transmission, reflection, and absorptive electromagnetic intensity as a function of wavelength of the ICE core. In one embodiment, the method includes varying e-beam or ion-beam intensities and strengths to control the shape of the ICE core.

18 Claims, 7 Drawing Sheets

(51) Int. Cl.
  *C23C 14/26*     (2006.01)
  *C23C 14/50*     (2006.01)
  *C23C 14/54*     (2006.01)
  *C23C 16/04*     (2006.01)
  *G01N 21/31*     (2006.01)
  *C23C 16/458*    (2006.01)

(52) U.S. Cl.
  CPC ............ *C23C 14/26* (2013.01); *C23C 14/505* (2013.01); *C23C 14/54* (2013.01); *C23C 14/541* (2013.01); *C23C 16/042* (2013.01); *C23C 16/4588* (2013.01); *G01N 21/31* (2013.01)

(58) Field of Classification Search
  CPC . C23C 16/042; C23C 16/4588; E21B 47/123; G01B 11/0625; G02B 5/28
  See application file for complete search history.

(56) References Cited

U.S. PATENT DOCUMENTS

| | | |
|---|---|---|
| 6,839,176 B2 | 1/2005 | Buchsbaum et al. |
| 6,913,938 B2 | 7/2005 | Shanmugasundram et al. |
| 7,082,345 B2 | 7/2006 | Shanmugasundram et al. |
| 7,138,156 B1 * | 11/2006 | Myrick ................. G02B 5/285 427/10 |
| 7,195,797 B2 | 3/2007 | Mearini et al. |
| 7,324,865 B1 | 1/2008 | Sonderman et al. |
| 7,465,681 B2 | 12/2008 | Hart et al. |
| 8,760,644 B2 | 6/2014 | Seckar |
| 2002/0012746 A1 * | 1/2002 | Mearini ................. B82Y 10/00 427/164 |
| 2002/0132063 A1 | 9/2002 | Watanabe et al. |
| 2003/0168613 A1 * | 9/2003 | Lee ....................... B82Y 10/00 250/492.1 |
| 2003/0176124 A1 | 9/2003 | Koike et al. |
| 2011/0262656 A1 | 10/2011 | Nagae et al. |
| 2016/0032718 A1 | 2/2016 | Jones et al. |
| 2016/0084068 A1 | 3/2016 | Pelletier et al. |
| 2016/0139085 A1 | 5/2016 | Pelletier et al. |

FOREIGN PATENT DOCUMENTS

| | | | |
|---|---|---|---|
| WO | 2012027442 | 3/2012 | |
| WO | 2013162914 | 10/2013 | |
| WO | WO-2013162914 A1 * | 10/2013 | ............ G01K 13/00 |
| WO | 2016108918 | 7/2016 | |

* cited by examiner

US 10,358,714 B2

SYSTEM AND METHOD FOR DEPOSITION OF INTEGRATED COMPUTATIONAL ELEMENTS (ICE) USING A TRANSLATION STAGE

TECHNICAL FIELD

The present disclosure relates generally to the thin film deposition, and more particularly, to systems and methods for deposition of integrated computational elements (ICE) using a translational stage.

BACKGROUND

When light interacts with matter, the light carries away information about the physical and chemical properties of the matter. A property of the light, such as intensity, may be measured and interpreted to provide information about the matter with which the light interacted.

Multivariate optical computing (MOC) is a powerful predictive spectroscopic technique that incorporates a multi-wavelength spectral weighting directly into simplified analytical instrumentation to provide a measure of a property of interest within a test sample. This is in contrast to traditional predictive spectroscopic techniques where a spectrum of a test sample is first collected, then digitized and post processed with a computer to correlate spectral signal with analyte concentration. MOC components require exact manufacturing compositions, depositions, and processes to function properly which may be very time intensive, expensive, and difficult to monitor and manage.

BRIEF DESCRIPTION OF THE DRAWINGS

Illustrative embodiments of the present invention are described in detail below with reference to the attached drawing figures, which are incorporated by reference herein and wherein.

DETAILED DESCRIPTION OF THE DRAWINGS

The illustrative embodiments provide a system and method for thin film deposition including controlling the generation or manufacturing of integrated computational elements (ICE) Cores for detecting a number of properties in a test sample. As used herein the terms "manufacture" or "manufacturing" are defined as making, producing, generating, fabricating, growing, and/or creating ICE Cores in accordance with the disclosed embodiments. ICE Cores are one embodiment of a multivariate optical computing device, system, or component for analysis of a test sample. The test sample may represent any combination of liquids, gasses, slurries, mods, polymers, multiphasic materials, hydrocarbon fluids, powders, and solids. The ICE Cores may be utilized on testing samples in any number of phases, such as solids, liquids, gases, slurries, emulsions, powders, and multi-phase solutions.

The ICE Cores may also be utilized in any optical mode, such as transmission, reflection, total internal reflection, fluorescence, Rayman, Raleigh scattering, Brillion scattering, fiber optic, distributed fiber optic, and so forth. The ICE Cores may have the same accuracy as laboratory quality optical spectrometers without using spectra, spectrometers, or conventional notch filters. In one embodiment, the ICE Cores may perform a specific calculation/regression to detect and/or quantify a specific analyte of interest, or characteristic, of a given test sample. The ICE Cores may be utilized nondestructively, non-invasively, in situ, and/or in real-time. For example, the ICE Cores may be utilized in harsh environments, such as downhole conditions of a wellbore. In addition, the ICE Cores may also be utilized in laboratories, mobile equipment centers, impromptu workstations, or other locations or environments.

In one embodiment, the deposition processes that control the optical function of the ICE Cores may be measured and controlled in real-time. For example, the ICE Core fabrication system may utilize sensors, such as crystal monitors, optical monitors, in-situ spectrometers, and in-situ ellipsometers. The optical function of the ICE Core may be defined as the electromagnetic intensity (e.g., transmission, absorption, and reflection) of the ICE Core as a function of wavelength. In one embodiment, ion assisted electron beam (e-beam) deposition may be utilized for each layer or step of the deposition process.

Additionally, the disclosed embodiments may include a system and method for translating a position of a thermal source (e.g., silicon or silicon dioxide (silica)) and/or a substrate holder that may be used in conjunction with or separate from the disclosed ion assisted electron beam deposition process.

Figure 1:
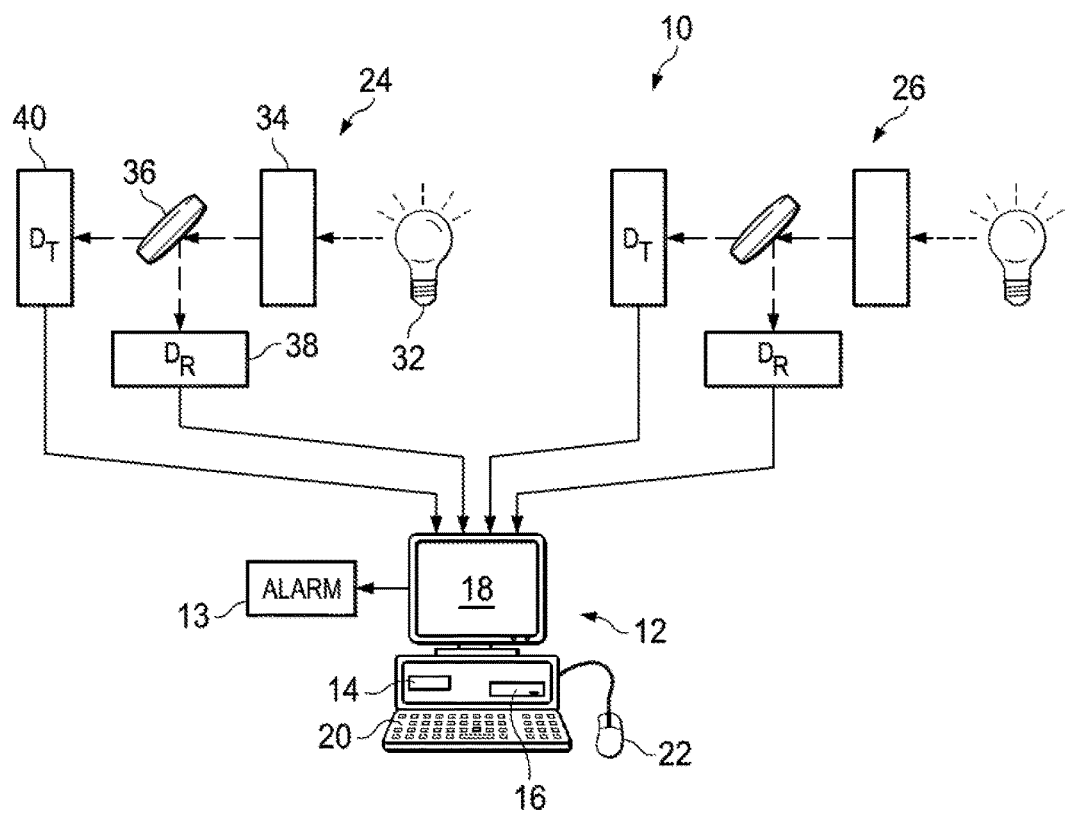
FIG. 1 is a schematic diagram of a system for monitoring test samples in a natural resource environment employing an in situ optical analysis device in accordance with an illustrative embodiment.

FIG. 1 is a schematic diagram of a system 10 for monitoring test samples in a natural resource environment employing in-situ optical analysis device in accordance with an illustrative embodiment. In one embodiment, the system 10 may be utilized to determine a number of properties of test samples (e.g., crude petroleum, water, mixtures, liquids, etc.) either down hole in a drilling well, laboratory, pipeline, or other environment. The term "down hole" means located in a well or a stream connected to a well or connected to any of one or more reservoirs whose fluids are subject to being pumped to the surface at a well. In practice, numerous reservoirs may be interconnected by a web of streams all feeding a common well head. The term pipeline means a pipe employed to convey petroleum from a field well head to a remote location. Pipes are employed down hole and in pipelines. The term "pipe" includes down hole pipes or pipeline pipes. Down hole pipes may be vertical, horizontal, or have other spatial relationships.

The determined properties may be utilized for analysis, to determine petroleum flow, or analysis of applicable mixtures and materials, and other relevant determinations. As used herein, the term "property" means chemical or physical characteristic, composition, properties, or elements contained in the test sample (i.e., petroleum or which forms the petroleum composition and which includes, but is not limited to SARA (saturates, asphaltenes, resins, aromatics) composition and content, solid particulate content such as dirt, mud, scale and similar contaminants, porosity, pH, total dissolved solids, ionic content (i.e., $H_2O$ ion-composition and content), hydrocarbon composition and content, gas composition C1-C6 and content, $CO_2$, $H_2S$ and correlated PVT properties including GOR (gas-oil ratio), bubble point, density, particle shape, particle distribution, and viscosity among other properties. For example, crude petroleum may include aromatics, resins, asphaltenes, and saturates.

System 10 may include apparatuses located at and in contact with flowing crude petroleum and which components are located down hole or on a pipeline to determine in real-time the properties of the petroleum which is flowing in pipes underground or in the pipeline. As a result, the apparatuses of the system 10 are subject to the extreme temperatures and pressures of the underground streams, but yet do not employ costly spectroscopic instruments as used in the prior art system, but rather rugged reliable optical analysis devices, such as ICE Cores. In another embodiment, the system 10 may be utilized for non real-time analysis of test samples in a mobile or home facility, sample container, or other location or container after retrieval of the test sample.

In one embodiment, system 10 may include a computer 12 including a microprocessor 14, memory 16 which may include one or more static or dynamic memories or caches (e.g., hard drive, ROM, RAM, etc.) for storing the analysis program and operating system program and determined data among other information as known in the art of spectral analysis as understood by one of ordinary skill. The computer 12 may include a display 18, a keyboard 20, and a mouse 22.

The microprocessor 14 may be circuitry or logic enabled to control execution of a set of instructions. The processor 14 may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks. The processor 14 may be a single chip or integrated with other computing, communications, exploration devices, down hole tools.

The memory 16 may be a hardware element, device, or recording media configured to store data for subsequent retrieval or access at a later time. The memory 16 may be static or dynamic memory. The memory 16 may include a hard disk, random access memory, cache, removable media drive, mass storage, or configuration suitable as storage for data, instructions, and information. In one embodiment, the memory 16 and processor 14 may be integrated. The memory may use any type of volatile or non-volatile storage techniques and mediums.

In one embodiment, the computer may be located at central location remote from the remainder of the system 10 comprising optical petroleum property sensing and optical analyzing devices 24 and 26. While two devices are shown, this number of devices is by way of illustration and more or fewer devices may be used in practice. For example, each optical analyzing device 24 and 16 may be utilized for detecting and analyzing light interacted with the associated sample or mixture, such as petroleum with varying properties of interest. The optical analyzing devices 24 and 26 may each measure multiple properties or a single property as needed. The optical analyzing devices may be utilized in combination to provide an overall picture of the condition of the petroleum and the location.

The optical analyzing devices 24 and 26 are rugged and may be configured to withstand the temperatures and pressures in-situ at the pipes and thus are emplaced for short term, long term, or permanent use. The optical analyzing devices 24 and 26 are a marked improvement over present analyzing systems which are not rugged, are not automatic and are not for relatively long term use. The optical analyzing devices 24 and 26 may be specifically manufactured to test and analyze one or more properties of a test sample. In other embodiments, the optical analyzing devices 24 and 26 may be manufactured for one time, temporary, or disposable use.

The number of optical analyzing devices 24 and 26 is arbitrary and is not intended to convey any significance. The number of optical analyzing devices 24 and 26 in the system 10 depends on the needs of one or more users, required analysis, the number of pipes/wells, and the number of properties being monitored. Communications within the system 10 may occur in real-time or via any number of subsequent communications, data transfers, or synchronization processes. A user may also initiate a communication, test, analysis, or other process using the system 10.

It is contemplated that the number of optical analyzing devices 24 and 26 of a system 10 is not limited to measuring the properties of a test sample at a single location. The computer 12 may be programmed to communicate with or monitor a large number of optical analyzing devices 24 and 26 associated with and located in respect of a number of different locations. Thus the properties of a test sample flowing independently in different location may be monitored simultaneously by one computer 12 which may also be programmed to correlate a number of different properties as being related to a flow assurance problem in one reservoir system. The computer 12 may represent one or more computing or communications devices, systems, equipment, or components.

The communications within the system 10 may occur directly or through one or more networks including, a publicly switched telephone network, cell or wireless networks (e.g., 3G, 4G, LTE, PCS, GMSR, etc.), Ethernet networks, or so forth. The computer 12 may also be coupled to an alarm output device 13 which may provide an audible alarm, a visual alarm or both.

In one embodiment, the computer 12 may monitor pipes, streams, reservoirs, and well bores to give a picture of the petroleum and other test samples flowing, stored, or being retrieved. As a result, the optical analyzing devices may monitor a number of properties instantaneously or at the convenience of one or more users. As a result, problems or issues may also be efficiently monitored, detected, and logged to take any number of corrective actions for a reservoir, stream, pipeline, or so forth. One or more thresholds may be utilized for distinct properties to perform more thorough analysis or perform different tests.

The optical analyzing devices 24 and 26 may be relatively low cost and rugged and may be implemented in many more locations and streams than otherwise possible with other systems. In one embodiment, the optical analyzing device 24 (described as a representative device) may include a light source 32, a test sample 34 being monitored, an ICE Core 36 operating an optical regression calculation device, a detector 38 for detecting light reflected from ICE Core 36, and a detector 40 for detecting the light transmitted by ICE Core 36. The ICE Core 36 may be a unique optical calculation device that includes multiple layers specially sized, shaped, and configured to determine properties of the test sample.

Figure 2:
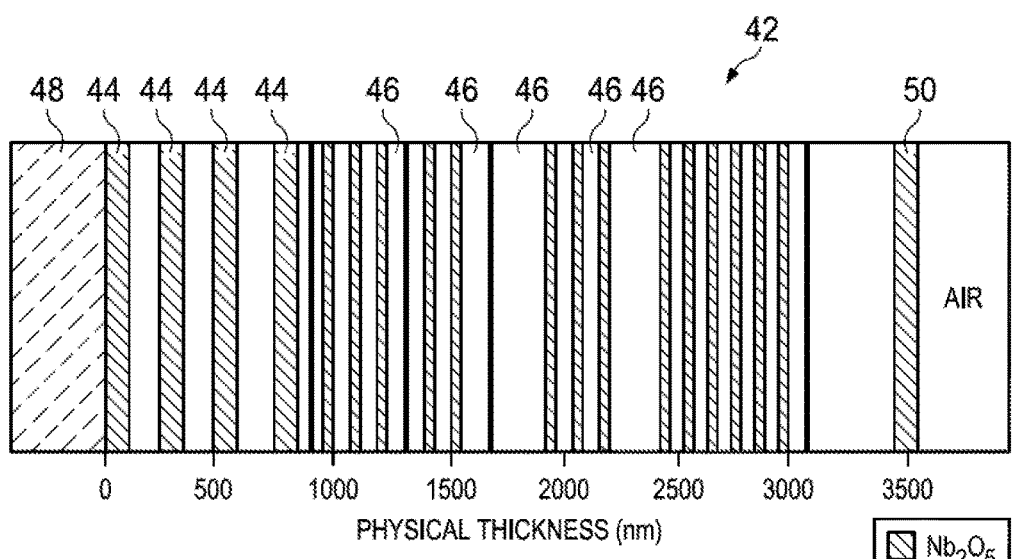
FIG. 2 is a side elevation sectional view of an ICE Core in accordance with an illustrative embodiment.

FIG. 2 is a side elevation sectional view of an ICE core 42 in accordance with an illustrative embodiment. In FIG. 2, the ICE core 42 may include a number of alternating layers 44 and 46 respectively of $Nb_2O_5$ and $SiO_2$ (quartz). In one embodiment, the layers 44 and 46 may be deposited on a glass substrate 48 such as, but not limited to, silicon or silica. The other end layer 50 of the optical calculating layers may be exposed to the environment of the installation. The number of layers and the thickness of the layers may be determined from and constructed from the spectral attributes determined from a spectroscopic analysis of a property of a sample mixture using a conventional spectroscopic instrument. In one embodiment, the combination of layers corresponds to the signature of the property of interest according to the spectral pattern of that property. The layers of the ICE Core 42 may be automatically controlled and deposited to correspond to the signature of the property.

The spectrum of interest of a given property typically includes any number of different wavelengths. The ICE Core 42 is provided for illustrative purposes only. The number of layers and their relative thicknesses of the ICE Core bear no correlation to any sample property to which the illustrative embodiments are directed, is given for comprehension purposes only, and are also not to scale. The thickness of the layers may be in the order of microns or nanometers.

The multiple layers and substrate have different complex indices of refraction. By properly selecting the materials of the substrate and layers and the layer thickness and spacing, the optical analysis device may be manufactured to selectively pass predetermined fractions of light at different wavelengths. Each wavelength is given a predetermined weighting or loading factor. The thicknesses and spacing of the layers may be determined using a variety of approximation methods from the spectrograph of the property of interest. The weightings that the ICE Core 42 layers apply at each wavelength are set to the regression weightings described with respect to a known equation, or data, or spectral signature as are known in the art. The ICE Core 42 processes the input light beam into the optical calculation device by optically weighting the input light beam to the desired loaded regression vector weightings for each wavelength. The ICE Core 42 output light intensity is measured by an optical transducer. The optical transducer converts the intensity of processed light from the ICE core to a signal that is directly related to and is proportional to the desired sample property. The optical transducer output signal represents the summation of all of the weighted intensities of the passed wavelengths from the ICE core and is the dot product of the input light beam and the ICE core regression vector.

These wavelengths may be weighted proportionately by the construct of the corresponding optical analysis device layers. The resulting layers together may produce an optical analysis device, such as ICE Core 42 that outputs modifies light intensity from the input beam. The transmitted and reflected light intensities, as measured by detectors 38 and 40 and processed by computer 12, represent the dot product of the input light and the loaded vectors of that property (e.g., resin). For example, the output optical analysis device intensity value is proportional to the amount of resin in the crude petroleum being examined. In this way, an ICE Core is produced for each property to be determined in the test sample.

Such ICE cores represent pattern recognition devices and components which produce characteristic output patterns representing a signature of the spectral elements that define the characteristic or property of interest. The intensity of the light output is a measure of the proportional amount of the characteristic in the test sample being evaluated. In one embodiment, outputs from a number of ICE cores in the form of electrical signals may be utilized to represent the characteristic or property of interest in the test sample.

There is good correlation between the predicted characteristic such as aromatics, for example, and the measured amount of characteristic. Thus, a system and method has been described for determining at least one characteristic of the test sample that may include causing the test sample to produce interacted light from incident light; performing a regression calculation or other processing on the interacted light with an optical analysis device responsive to the interacted light incident thereon to produce at least one output signal manifesting the calculation and the corresponding at least one property; and determining the at least one property of the test sample from the at least one output signal.

Figure 3:
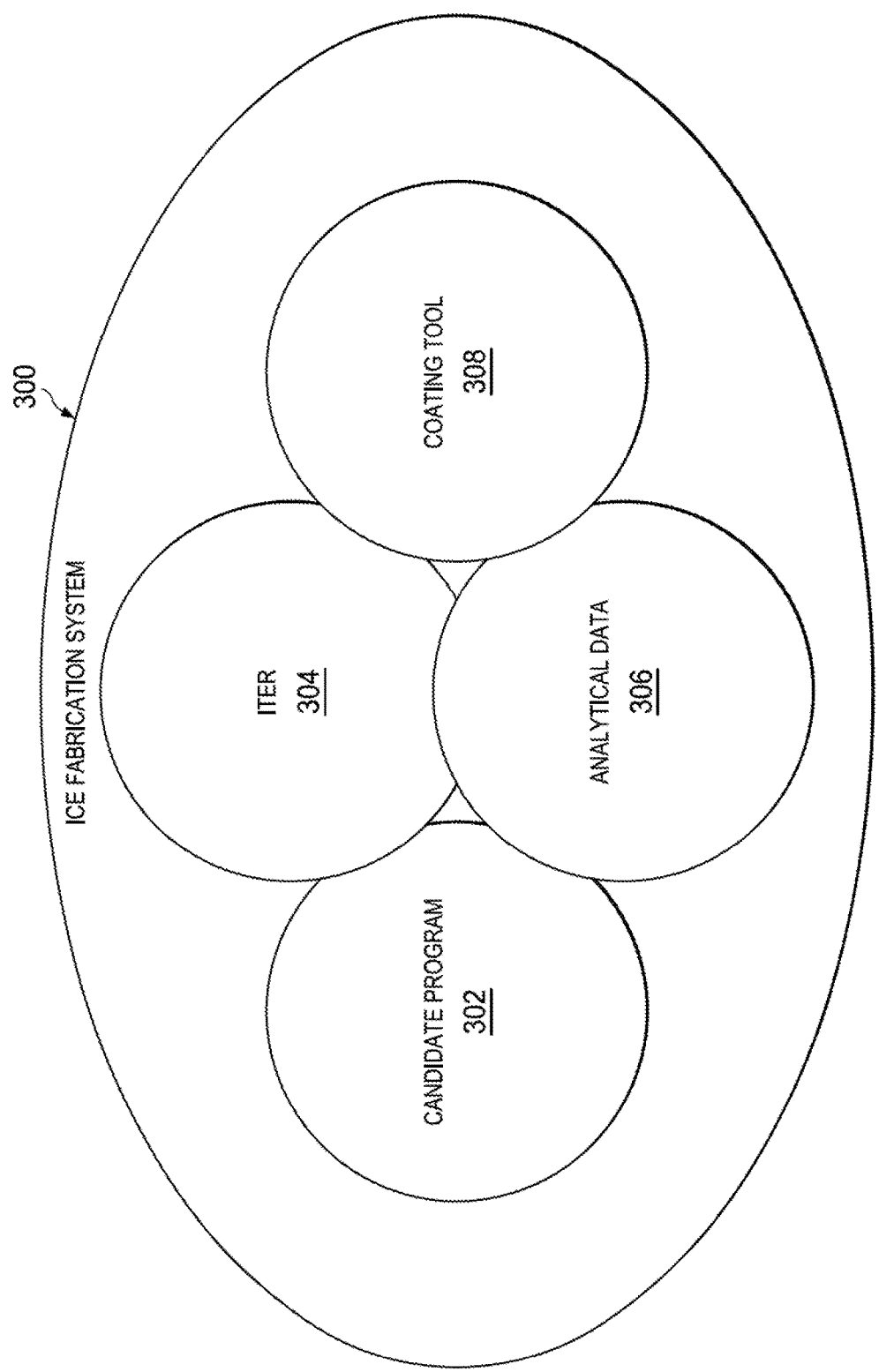
FIG. 3 is a pictorial representation of an ICE Core fabrication system in accordance with an illustrative embodiment.

FIG. 3 is a diagram of an ICE Core fabrication system 300 in accordance with an illustrative embodiment. The ICE Core fabrication system 300 may include any number of hardware, software, and firmware components. In one embodiment, the ICE Core fabrication system 300 may include a candidate program 302, iteration application (ITER) 304, analytic data 306, and a coating tool 308 that communicate directly or indirectly through one or more networks. The ICE Core fabrication system 300 may include any number of software modules, applications, or logic configured to execute a set of instructions as described herein.

In one embodiment, the ICE Core fabrication system 300 may also include any number of servers, databases, routers, terminals, semiconductor manufacturing tools, peripherals, or so forth.

In one embodiment, the candidate program 302 may be configured to create filter information for the ICE Cores. For example, the candidate program 302 may utilize analyte concentration data, and substrate and material complex indices of refraction information (n, k), to determine layer properties. Manufacturing of various ICE Cores may require recently obtained optical constraints to formulate the materials deposited in the different layers of the ICE cores, the thickness, treatments of individual layers, and other applicable information. The optical constraints may be sent and received automatically or in response to user interaction.

ITER 304 may be a multi-application group of compiled programs that communicates with the coating tool 308 and optimizes filter designs based on feedback from the candidate program 302. For example, the ITER 304 may enable optimization and/or automation of the deposition process such as pseudo layer control and modification and/or allowing slack layer additions required to yield a filter.

The analytical data 306 may be data acquired from multiple locations within the manufacturing chamber. The analytical data 306 may be acquired by optical monitors, spectrometers, ellipsometers, thermometers, barometers, gas sensors, quartz crystal microbalances, thermometers, or other measuring or monitoring equipment internal or external to the ICE core fabrication system 300. The analytical data 306 may be modeled and processed as consistent with the filter run objectives.

The coating tool 308 may be a manufacturing tool for controlling and depositing each layer. In one embodiment, the coating tool 308 is a thin film deposition production system. The coating tool 308 may be configured to perform different deposition processes, such as thermal induction evaporation, ion-assisted thermal induction evaporation, RF bias clean, magnetron sputtering, and plasma enhanced CVD. The coating tool 308 may include an isolated process chamber configured to apply a vacuum to the ICE Cores as they are manufactured. In one embodiment, the coating tool 308 may utilize trigger thresholds and may wait for a reply.

Figure 4:
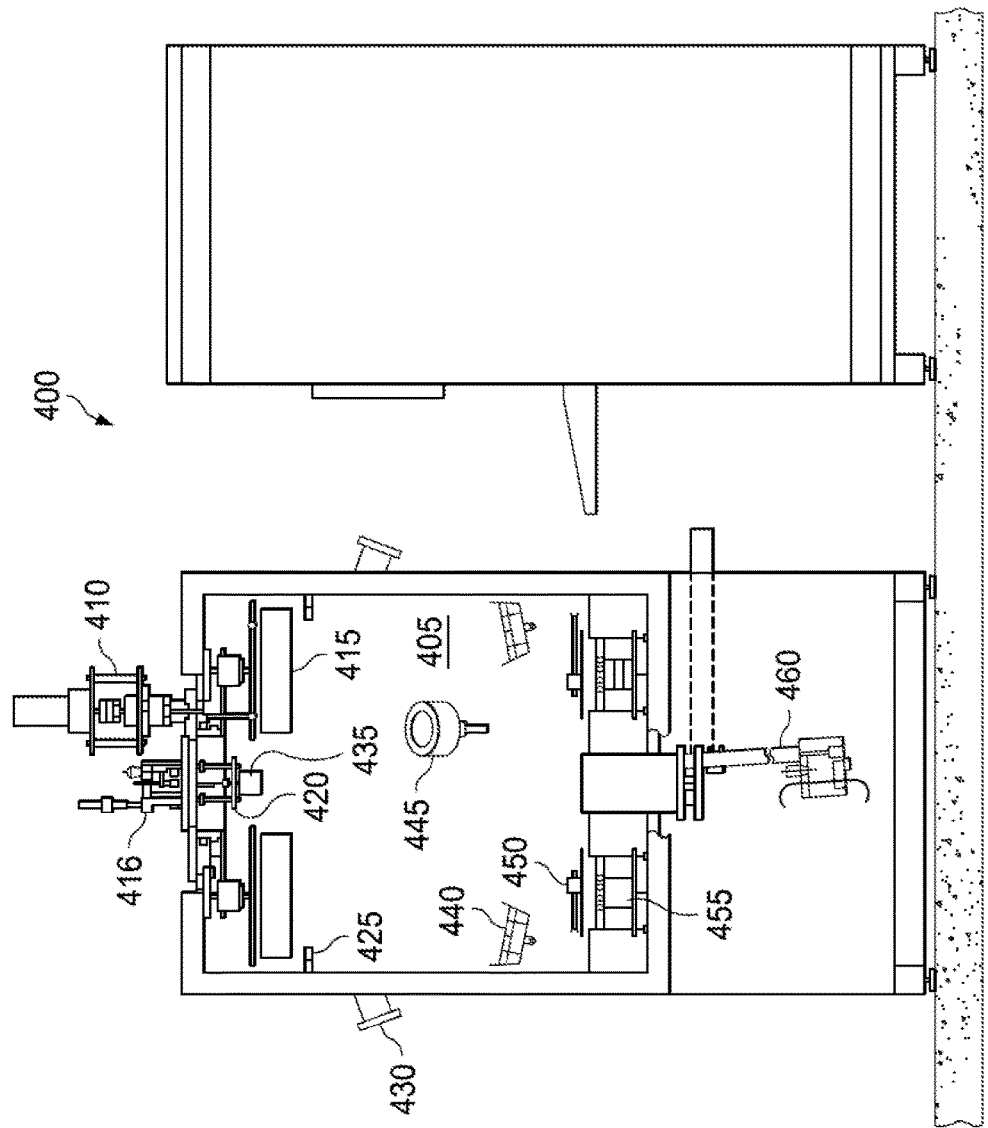
FIG. 4 is a diagram of an ICE Core fabrication system in accordance with an illustrative embodiment.

FIG. 4 is a schematic view of one example of an ICE Core fabrication system 400 in for manufacturing ICE Cores in accordance with the disclosed embodiments. For example, in one embodiment, the ICE Core fabrication system 400 may be utilized to perform thin-film deposition to manufacture ICE Cores. Any number of physical vapor deposition (PVD) and chemical vapor deposition (CVD) may be utilized. In one embodiment, the ICE Core fabrication system 400 may include a vacuum chamber 405, a planetary drive 410, one or more planetary assemblies 415, a spectrometer 416, shuttered sensors 425, ellipsometer ports 430, quartz heaters 440, an ion source 445, source shutters 450, one or more thermal sources (e.g., e-beam sources 455, thermal evaporation sources, etc.), and an optical monitor assembly 460. In one embodiment, the ICE Core fabrication system 400 may be connected to one or more computing devices for managing the various components and the layers deposited on a substrate.

In one embodiment, the ICE Core fabrication system 400 may be configured to control deposition of a number of layers and properties of the layers. For example, the properties of the layers that may be controlled may include at least an index of refraction, optical absorption coefficient, physical thickness, and optical thickness. In one embodiment, the ICE Core fabrication system 400 may utilize a regression vector to establish the transmission, reflection, and absorption functions of the ICE Cores before, during, and after generation. The ICE Core may vary in thickness and layers. For example, the ICE Core may vary between approximately 5 nm and approximately 50 μm and may have between approximately 2 and approximately 50 layers. However, in other embodiments, the thickness may be increased and decreased based on application, a single layer may be utilized or an extremely large number of layers may be used based on very complex applications of the ICE Core.

In one embodiment, the vacuum chamber 405 may be a rigid enclosure in which air or other gases are removed by a vacuum pump (not shown). The vacuum chamber 405 may include any number of ports allowing distinct components, such as instruments, sensors, sources, gas sources, and so forth, to be grounded to or installed within the vacuum chamber 405 for utilization during the ICE Core fabrication process. The vacuum chamber 405 may be formed of metals, such as stainless steel, aluminum, mild steel, or brass, high-density ceramics, glass, acrylics, and other materials suitable for the different elements and mixtures deposited and utilized within the vacuum chamber 405. In another embodiment, an evaporation cloud emitted within the vacuum chamber 405 may be masked to enhance uniformity of deposition. Masking is accomplished, but is not limited to, metal shields before the planetary assembly 415 with apertures allowing the evaporation cloud to pass to the planetary assembly 415. The vacuum chamber 405 may also vary the pressure within the vacuum chamber as necessary for each step in the process. The vacuum chamber 405 may introduce any number of background or reactant gases during the process.

The vacuum chamber 405 may include any number of supports, ports, adapters, interfaces, or so forth. The vacuum chamber 405 may include any number of electrical, gas, suction, disposal, or other inputs or outputs. For example, the background gases utilized within the vacuum chamber 405 may be varied based on the deposition or other process being performed upon the substrates/ICE Cores. The vacuum chamber 405 may also include any number of other securing panels, assemblies, or so forth. For example, the vacuum chamber 405 may include leveling feet to ensure the vacuum chamber 405 is maintained level as well as any number of peripherals, such as keyboards, displays, a mouse, touchscreen, or so forth.

In one embodiment, the planetary drive 410 may be a motion device or system for moving a planetary system with at least one planetary assembly 415 holding substrates or ICE Cores during the manufacturing process. The planetary assembly 415 may also be referred to as a substrate platen. The planetary drive 410 may represent a single or multi component planetary mechanism. In some embodiments, the planetary drive 410 may be configured to move in three dimensions. For example, the planetary drive 410 may rotate as well as tilt to provide motion along three different axes. In one embodiment, the planetary drive 410 may include one or more motors, and a gearbox including, for example, a central or "sun" gear which engages with a number of surrounding or planet gears. The planet gears may be held in place by a cage or carrier that fixes the planet gears in orbit relative to each other. In one embodiment, each of the individual planets within the planetary assembly 415 is individually rotatable on their respective axis as well as tilt to provide motion along three different axes. The one or more motors may smoothly rotate the planetary assembly. For example, the ICE Cores may be rotated as each new layer is deposited to ensure uniform deposition. The planetary drive 410 and the planetary assembly 415 provide stability, rotational stiffness, and consistent rotational speeds for utilization in the ICE Core manufacturing process.

In one embodiment, the planetary drive 410 may move the planetary assembly 415, and/or the individual planets within the planetary assembly 415, and the corresponding substrates/ICE Cores during deposition to increase uniformity in the ICE Cores. For instance, in one embodiment, the ion source 445 and the e-beam sources 455 may also be moved during deposition or other processes (e.g., secondary planetary drive systems). For example, a distance between the substrate attached to the planetary assembly 415 (or other types of substrate holder) and the thermal source (e.g., e-beam sources 455) may be varied during deposition to affect the shape of the ICE Cores for improving uniformity of the deposited material. Rotating one or more of the planetary assembly 415, ion source 445, and the e-beam sources 445 may be utilized to maximize the uniformity, density, and to compensate for the point source nature of the evaporation plume from the e-beam source 455. As an example, in one embodiment, the thermal source may move in the x, y, and/or z direction relative to the substrate holder, while the substrate holder maintains its normal position or movement. The x-direction is movement from side to side, the y-direction is movement from front to back, and the z direction is up and down movement. In certain embodiments, the movements may be predetermined prior to the deposition process to improve uniformity of the ICE core.

Alternatively, in some embodiments, the thermal source may move in the x, y, and/or z direction relative to the substrate holder, while the substrate holder and/or individually controlled sections of the substrate holder (e.g., one or more planets in the planetary assembly 415) may also move in the x, y, and/or z direction, as well as tilt, relative to the thermal source to provide a more uniform deposition layer. Movement of both the thermal source and the substrate holder may be advantageous as the overall system can be smaller because each would only have to move a portion (e.g., half) of the desired distance. Movement of the substrate holder such as the planetary assembly 415 may include moving the outer planetary system while maintaining the normal position or not moving of the individual planets; moving the outer planetary system and moving the individual planets; moving the individual planets while not moving the outer planetary system; and moving only certain individual planets while not moving others. Again, each of the movements may be in the x, y, and/or z direction, as well as tilt, relative to the thermal source to provide a more uniform deposition layer.

Still, in some embodiments, the substrate holder and/or individually controlled sections of the substrate holder may move in the x, y, and/or z direction, as well as tilt, relative to a non-moving thermal source. Further, in some embodiments, the ion source 445 may also be moved to assist in creating a uniform deposition layer.

In certain embodiments, the ICE Core fabrication system 400 may preprogrammed to control the movement of the thermal source and/or the substrate holder based on the results of a trial and error process to determine the optimal movement/position of the thermal source and/or the substrate holder that yields the highest percentage of uniform ICE Cores. For example, the trial and error process may include moving the thermal source in only one direction relative to the substrate holder and assessing the quality of the produced ICE Cores, then moving the thermal source in two directions and assessing the quality of the produced ICE Cores, and then moving the thermal source in three directions and assessing the quality of the produced ICE Cores. Similarly, the trial and error process may also include moving only the substrate holder or a portion of the substrate holder relative to the thermal source in one, two, or three directions, and assessing the quality of the produced ICE Cores. Additionally, the trial and error process may also include moving both the thermal source and the substrate holder relative to one another, and assessing the quality of the produced ICE Cores. The exact movements (e.g., timing, distance, amplitude, frequency, etc.) may be adjusted during the trial and error process to determine the optimal movements that yields the highest percentage of uniform ICE Cores.

Additionally, in some embodiments, the ICE Core fabrication system 400 may be configured to stop/block or reduce the thermal source plume while moving the substrate holder and/or the thermal source. This may occur for a particular movement or during all movements. The movement may be subtle, rapid, on a linear stage, and/or rotated about an axis. Additionally, the movement may follow a random motion, sinusoidal motion, trapezoidal motion, and other types of dimensions.

Alternatively, or in addition to being preprogrammed based on the trial and error process described above, in some embodiments, the ICE Core fabrication system 400 may be configured to automatically control and adjust the movement of the substrate holder and/or the substrate holder during the deposition process based on real-time measurements obtained using one or more of the various components and sensors of the ICE Core fabrication system 400.

For instance, in one embodiment, the ICE Core fabrication system 400 may include a test glass changer 420 for securing an optical monitor test chip 435 for performing real-time analysis using the spectrometer 416, ellipsometers 430, and the optical monitor assembly 460. In one embodiment, the optical monitor assembly 460 may be configured to evaluate the performance of the ICE Core in situ. For example, the optical monitor assembly 460 may utilize any number of wavelengths to measure the transmittance, reflectance, and absorption of the ICE Cores during one or more of the manufacturing steps within the vacuum chamber 405. The spectrometer 416 may be configured to perform full spectrum analysis and real-time chamber characterizations. For example, the spectrometer 416 may be configured to control reflectance and transmittance of layers during thin-film deposition based on analysis of the optical monitor test chip 435. The vacuum chamber 405 can be configured to allow individual optical monitoring or combinations of optical monitoring. For example the ellipsometry measurements made with ellipsometer 430 can be made on a different optical monitoring chip 435 than that of the optical monitoring system 460. Alternatively, the optical monitoring system and the full spectrum measurement spectrometer 416 can be configured to monitor different optical monitor test chip 435.

The test glass changer 420 may be utilized to facilitate optically measuring layer properties of the optical monitor test chip 435. In one embodiment, the test glass changer 420 may be fixed in position. In another embodiment, the test glass changer 420 may connect to or move along with the planetary drive 410 and the planetary assembly 415. The test glass changer 420 in the optical monitor test chip 435 are configured to receive each of the layers or treatments introduced in the vacuum chamber 405 to monitor in real-time the deposition process.

The ellipsometer ports 430 are configured to receive one or more ellipsometers (not shown) for investigating the dielectric properties (complex refractive index or dielectric function) of thin films. The ellipsometers may be used to characterize composition, roughness, thickness (depth), crystalline nature, doping concentration, electrical conductivity, and other material properties. The ellipsometers are very sensitive to the change in the optical response of incident radiation that interacts with the material being investigated, such as the optical monitor test chip 435.

The quartz heaters 440 may represent any number of heating devices, components or elements. In one embodiment, the quartz crystals may be incandescent lamps filled with highly pressurized halogen gas and other elements utilized to protect a filament and increase longevity. The lamps may be made out of a quartz glass because of its hotter melting point than standard glass, thus the name quartz heaters 440. The quartz heaters 440 may emit infrared energy and may be particularly effective in the ICE Core system 400 due to their rapid heater response and high power density. The quartz heaters 440 may also be utilized to direct radiation in a uniform and concentrated pattern. In one embodiment, the quartz heaters 440 may control the temperature of the substrate within the vacuum chamber 405 in real-time to ensure proper deposition of materials as well as other process steps imposed upon the substrates connected to the planetary assembly 415.

In one embodiment, the ion source 445 may be an electro-magnetic device that is used to create charged particles. The source ions (i.e., gallium ions) generated by the ion source 445 may be focused broadly or narrowly onto the substrates and ICE Cores utilizing one or more electrostatic lenses. The ion source 445 may be utilized to assist thermal deposition. The ion source 445 may offer the advantage of extremely high deposition rates combined with the desired real and imaginary refractive index (n and k), Crystal stress reduction, and improve film adhesion compared with thermal deposition alone. The ion source 445 may also reduce total deposition times by as much as a factor of 30. Utilizing the ion source 445 may help control the density and crystal structure of the deposited material on the substrate. For example, any number of stresses and voids may be avoided as well as poor adhesion to the substrate, cracking the films, and varying optical properties may be avoided by utilizing the ion source 445. The ion beam emitted by the ion source 445 enables the condensing deposit material electrons to mobilize, thereby increasing the resultant density (and also real index of refraction) and material adhesion.

The n and k values of each layer of the ICE Core may be considered critical parameters. The ion source 445 may vary the intensity or strength in real time as an independent and highly accurate real-time fine tune control to obtain the desired optical properties of each layer of the ICE Core.

The e-beam sources 455 and the source shutters 450 may be utilized to perform electron beam physical vapor deposition (EBPVD). In one embodiment, the e-beam sources provide a system for elevating temperatures of a deposition material within the e-beam sources (e.g. a crucible or other container) for distribution into the vacuum chamber 405. For example, a high energy electron beam may be utilized to excite a deposition material that is released through the source shutters 450 which control the dispersion rate and pattern into the vacuum chamber 405. In one embodiment, the source shutters 450 may provide a regulator for controlling the deposition materials released from the e-beam sources 455. In addition to e-beam deposition, the ICE Core fabrication system 400 may be configured to perform resistive heating deposition, electromagnetic source deposition, and inductive heating deposition.

In one embodiment, the ion source 445 and the e-beam sources 455 may adjust at least one of the direction, power, intensity, and other parameters directed toward a substrate mounted on the planetary assembly 415 to control deposition and therefore transmission shape of the ICE Cores. The real time monitoring of the substrate utilizing the various sensors and measurement devices of the vacuum chamber 405 may be utilized to compensate for small derivations and drift and to maintain a desired transmission shape that may be associated with a target design. The utilization of e-beam and ion assisted e-beam deposition as described herein is unique for ICE Core manufacturing.

In one embodiment, the transmission values of the ICE Cores may vary as a function of wavelength utilized to perform the manufacturing processes. The various processes are distinct from other semiconductor processes utilized for interference, cut-off, or notch filters that limit information to that extractable relative to bandwidth in the optical spectrum. In one embodiment, the ICE Cores may be utilized to derive information that is in a greater resolution than the bandwidth utilized to take the readings with the ICE Cores. The increased resolution as compared to the bandwidth makes the ICE Cores and manufacturing processes unique.

The various components and sensors of the ICE Core fabrication system 400 may measure performance metrics to establish transmission, reflection, and absorption functions of the ICE Core during the manufacturing process. For example, the ion source 445 and the e-beam sources 455 may be actively managed and controlled to affect the transmission, reflection, and absorption function of the ICE Cores.

In accordance with the disclosed embodiments, the use of the ion assisted e-beam deposition process system may be used in conjunction with or separate from the disclosed system and method for translating a position of a thermal source and/or a substrate holder as described above.

In one embodiment, the batch to batch variability of the layer depositions and other processes may be tracked and recorded in one or more databases. As a result, the exact times, temperatures, voltage, current, compositions, intensities, distances, speeds, moisture, and other factors utilized by the ICE Core fabrication system 400 may be duplicated across a number of other ICE Core fabrication systems whether locally or remotely located to provide consistent results. Individual component variances may be recorded and duplicated as necessary.

Figure 5:
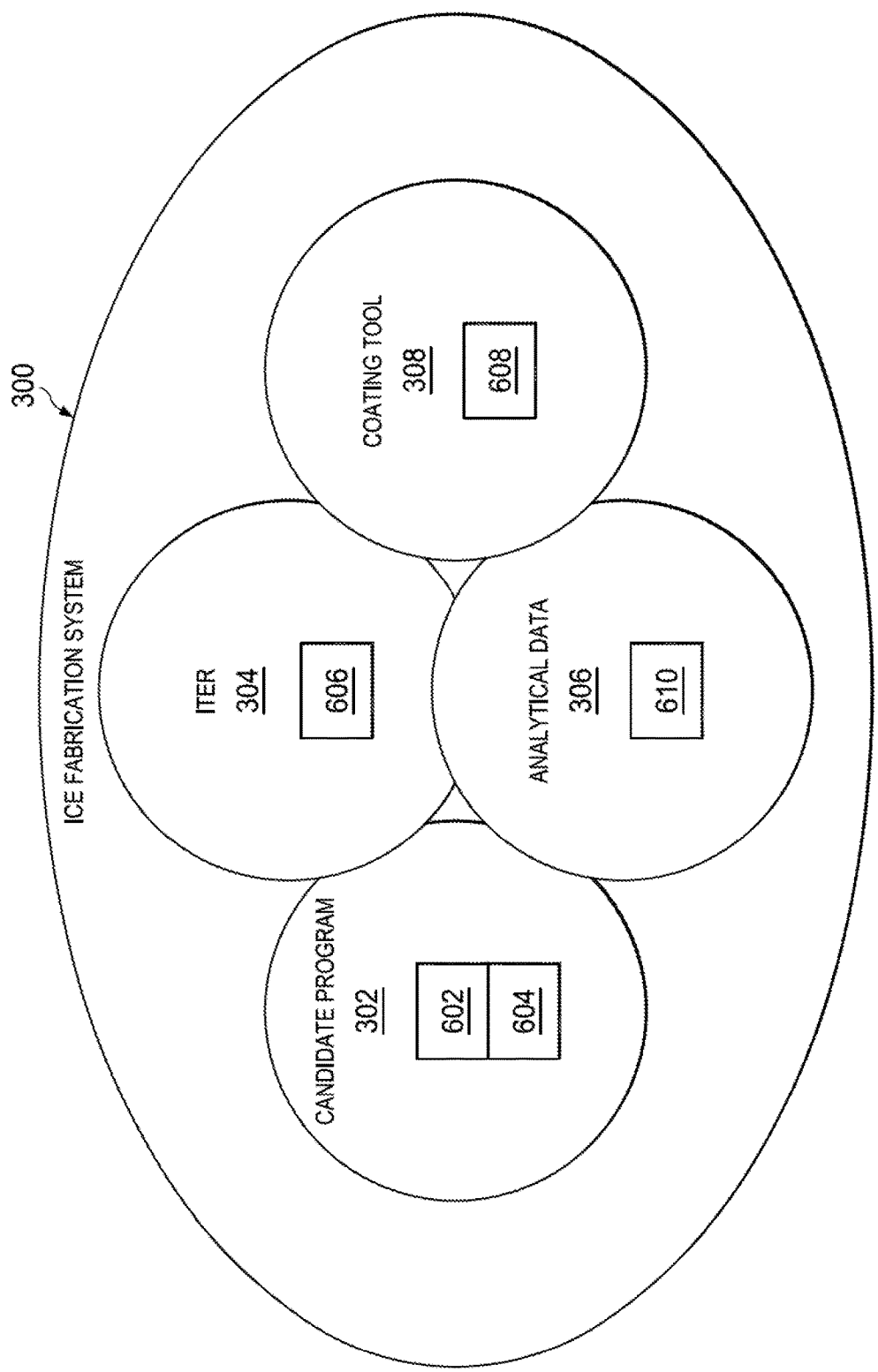
FIG. 5 is a pictorial representation of an ICE Core fabrication system in accordance with an illustrative embodiment.
Figure 6:
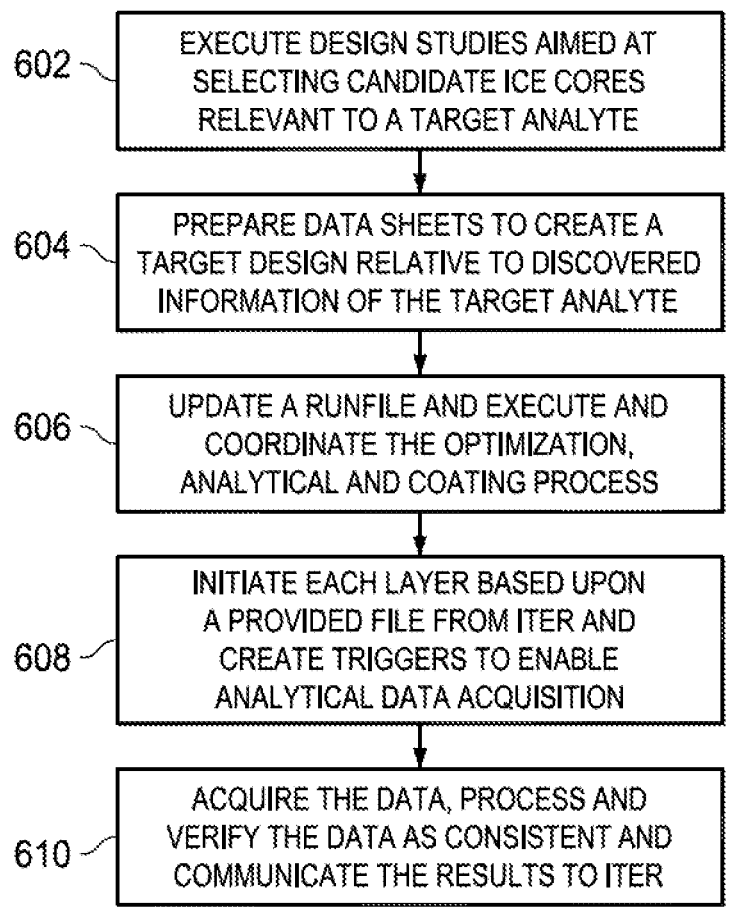
FIG. 6 is a flowchart of a process for preparing for fabrication of ICE Cores in accordance with an illustrative embodiment.

Turning now to FIG. 6, a flowchart of a process for preparing for fabrication of ICE Cores is presented in accordance with an illustrative embodiment. In one embodiment, the processes of FIG. 6-8 may be implemented by one or more components of an ICE Core fabrication system, device, or equipment, such as, but not limited to, the ICE Core fabrication system 300 depicted in FIG. 5.

In one embodiment, the process begins by executing design studies aimed at selecting candidate ICE cores relevant to the target analyte (step 602). For example, in one embodiment, candidate program 302, as depicted in FIG. 5, receives optical spectral data related to and containing the required information about the analyte for which the ICE Core is to be designed and fabricated. Typical target analytes include methane, ethane, propane and other organic and inorganic chemicals relevant to the exploration of hydrocarbons reservoirs. Candidate program 302 also receives optical material constant information (real and imaginary refractive indices) of the substrate and the materials used to fabricate the individual layers 44 and 46 of ICE Core 42. Candidate design studies (step 602) execute routines to generate many candidate ICE Core designs. The candidate design studies may also sort the many candidate designs based on a figure of merit (FOM) such as Standard Error of Calibration (SEC) or Mean Squared Error (MSE) between the calculated optical function of the candidate ICE Core and the desired loading regression vector.

In one embodiment, the target ICE Core design may be selected for the candidate design by an expert, scientist, or automated system based upon detailed calculations presented by the design study (step 602). The system then prepares data sheets to create a target design relative to discovered information of the target analyte (step 604). The data sheets include the required information to be passed to the fabrication system 300 to allow the fabrication process to commence, automated and optimized. The data sheets can contain, but is not limited to, or combinations of, the target design; planetary system, e-beam, ion beam control parameters; and optical monitoring, ellipsometer and spectrometer parameters.

Next, the process updates the runfile and executes and coordinates the optimization, analytical and coating process (step 606). The process may determine the initial parameters, settings, and conditions that may be used upon initialization. In one embodiment, the process may cycle data associated with the target design through one or more applications to determine parameters of the optimization, analytical, and coating process.

Then, the process initiates each layer based upon a provided file from ITER and creates triggers to enable analytical data acquisition (step 608). During step 608, one or more layers may be deposited upon the substrate or in process ICE Core. In one embodiment, the system may return to step 606 for each layer in an interactive process to initiate each layer.

Finally, the system acquires the data, processes and verifies that the data is consistent, and communicates the results to ITER (step 610). The data may be acquired utilizing any number of sensors, such as spectrometers, ellipsometers, cameras, temperatures, pressure and so forth. In one embodiment, the process may return again to step 606 based on the acquired data. For example, the system may be required to perform additional material deposition based on the acquired data.

Figure 7:
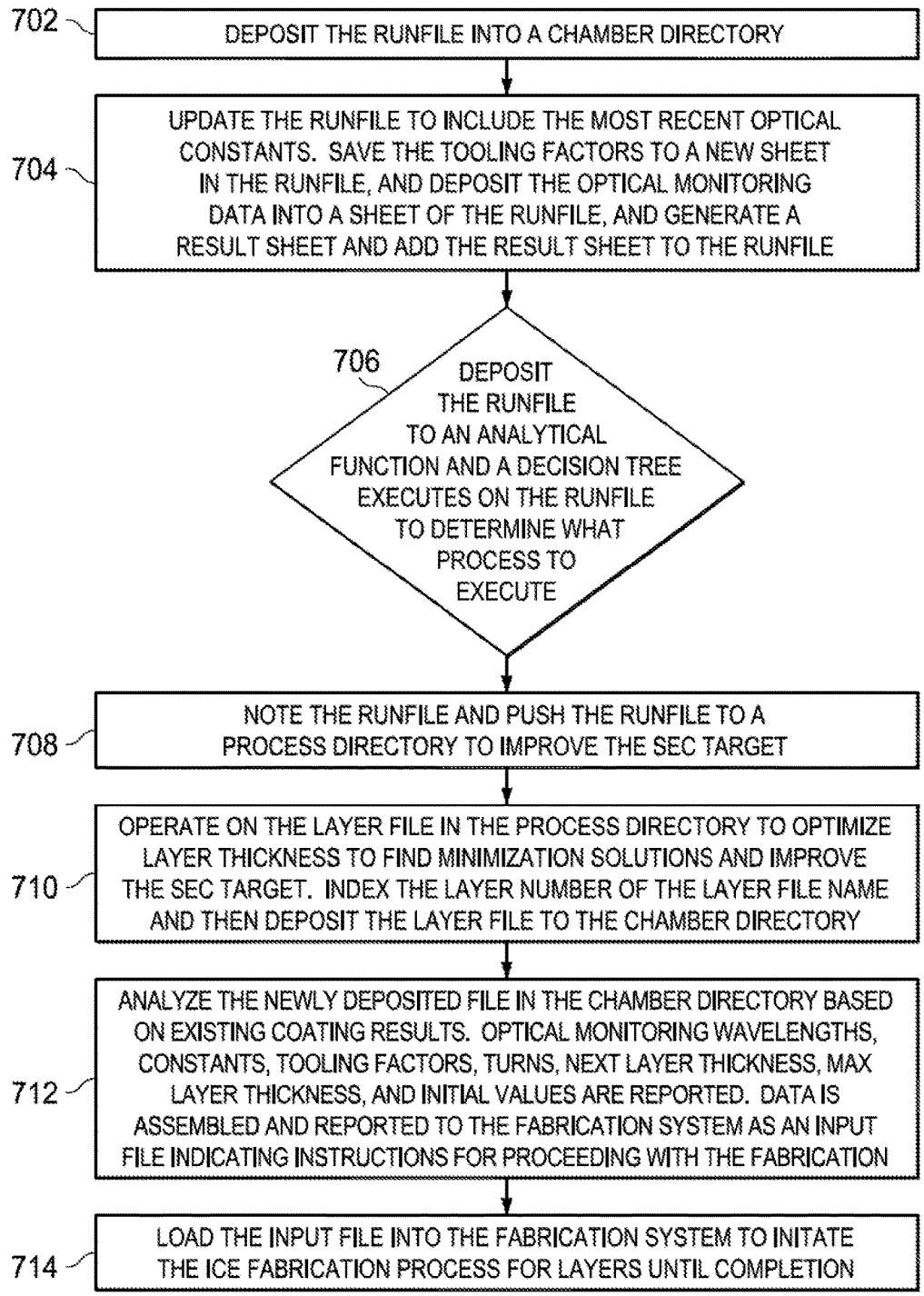
FIG. 7 is a flowchart of a process for preparing for fabrication of ICE Cores in accordance with an illustrative embodiment.

FIG. 7 is a flowchart of a process for preparing for fabrication of ICE Cores in accordance with an illustrative embodiment. The process of FIG. 7 may be performed for initial parameters (i.e., '0' layer file) and settings for the different components of the system.

In one embodiment, the system first deposits the runfile into a chamber directory (step 702). During step 702, the first layer spectrometer file is deposited into a spectrometer directory causing the initiation of the first layer process. The system then updates the runfile to include the most recent optical constants, saves the tooling factors to a new sheet in the runfile, deposits the optical monitoring data into a sheet of the runfile, and generates a result sheet and adds the result sheet to the runfile (step 704).

Next, the system deposits the runfile to an analytical function and a decision tree executes on the runfile to determine what process to execute (step 706). The analytical function may determine the properties of the ICE Core that are required to meet the target design. The system notes the runfile and pushes the runfile to a process directory (step 708). In one embodiment, the runfile may be pushed to improve the SEC target. The system operates on the layer file in the process directory to optimize layer thickness to find minimization solutions and improve the SEC target (step 710). The system also indexes the layer number of the layer file name and then deposits the layer file to the chamber directory (step 710).

The system then analyzes the newly deposited file in the process directory based on existing coating results. Optical monitoring wavelengths, constants, tooling factors, turns, next layer thickness, max layer thickness, and initial values are reported. Data is assembled and reported to the fabrication system as an input file indicating instructions for proceeding with the fabrication (step 712). In one embodiment, the newly deposited file is analyzed for SEC and delta/B. The optical constants to be used in ovonic memory switch (OMS) calculations may also be reported. During step 712 a decision may be made regarding the use of OMS or vibration monitoring may be made.

Finally, the system loads the input file into the fabrication system to initiate the ICE fabrication process for layers until completion (step 714). In one embodiment, the input file is the Hfile.

Figure 8:
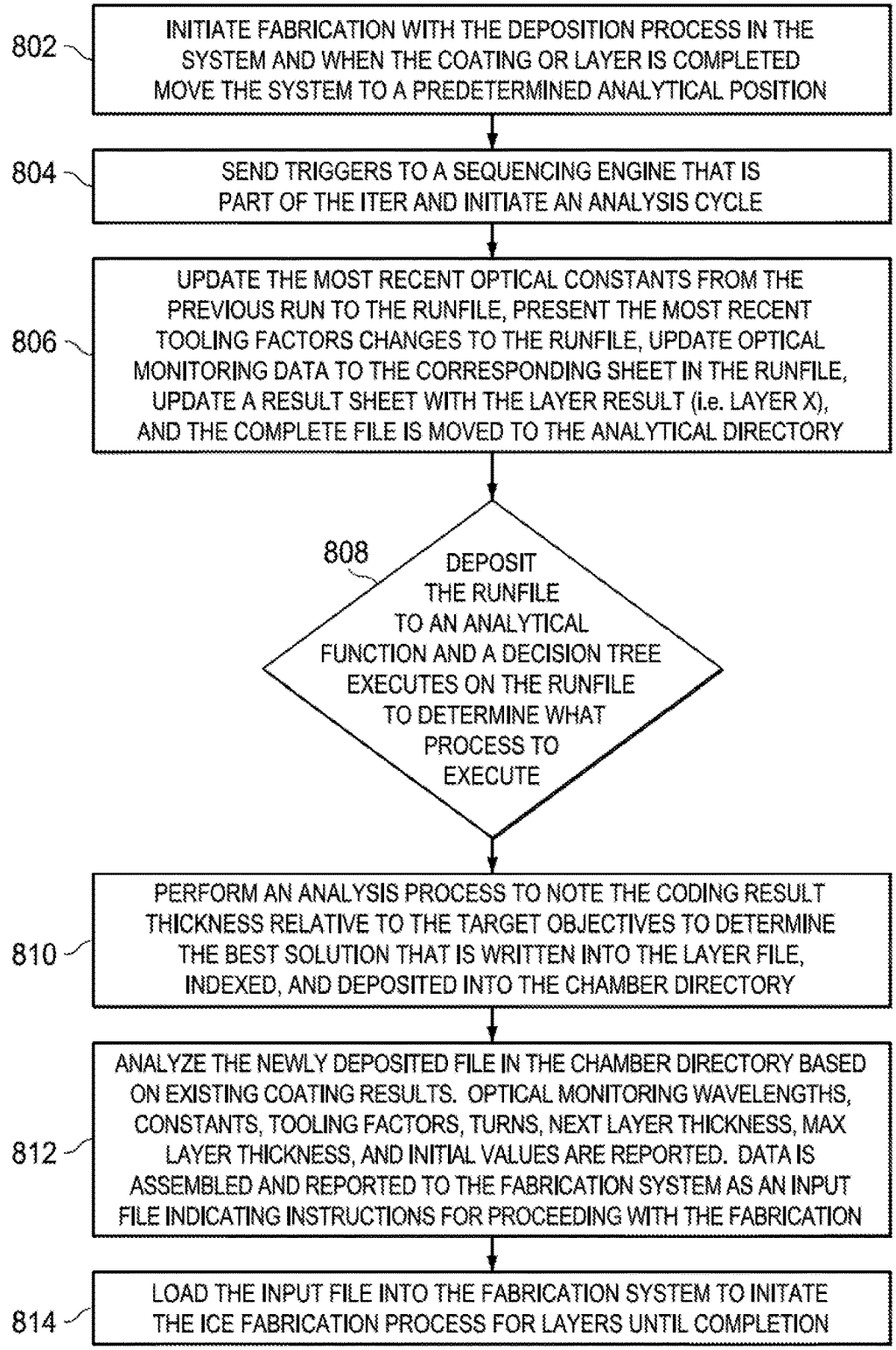
FIG. 8 is a flowchart of a process for performing fabrication of ICE Cores in accordance with an illustrative embodiment.

FIG. 8 is a flowchart of a process for performing fabrication of ICE Cores in accordance with an illustrative embodiment. In one embodiment, the process may begin by initiating fabrication in the system and when the coating or layer is completed, moving the system to a predetermined analytical position (step 802). The system, as previously described, may represent a closed loop control system.

Next, the system sends triggers to a sequencing engine that is part of the ITER and initiates an analysis cycle (step 804). During the analysis cycle of step 804, a number of trigger events and complete events may be executed via a predetermined sequence and the corresponding sequencing software. In coordination with the spectrometers and ellipsometers, data may be acquired, analyzed, and accumulated into a layer file (i.e. E_Layer_X—where X is the layer number) and presented to the spectrometer director for sequencing through the ITER applications.

The system then updates the most recent optical constants from the previous run to the runfile, presents the most recent tooling factors changes to the runfile, updates optical monitoring data to the corresponding sheet in the runfile, updates a result sheet with the layer result (i.e. layer X), and moves the complete file to the analytical directory (step 806).

The system deposits the runfile to an analytical function and a decision tree executes on the runfile to determine what process to execute (step 808). The system then performs an analysis process to note the coating results thickness relative to the target objectives and determines the suitability and the choices for the next step to be taken in the process (step 810). In one embodiment, the choices include the creation or non-creation of a pseudo layer where the filename would be indexed. If selected, the runfile may be appropriately modified to support the creation of the pseudo-layer and moved to the chamber directory. In another embodiment, the runfile may be moved onto the process directory for further activity as determined by the decision tree utilized in step 808.

In the depicted embodiment, the system performs an analysis process to note the coating result thickness relative to the target objectives to determine the best solution that is written into the layer file, indexed, and deposited into the chamber directory (step 810). In one embodiment, in the process directory, the target design is reported in the results of the coating activity are presented for operator review. The design file and the design number of the in process activity may be reported as well. Parallel computing may be implemented and the optimization tool may operate with verbose reporting provided. Each layer may be optimize to find minimization solutions (stepping in both directions) and further improve the standard error of calibration (SEC) relative to the target objectives. If decoding error is large and a solution cannot be accommodated (e.g. a coating error outside of 15% of the initial design target SEC) then further calculations may be executed. Solutions may be investigated whereby 'slack' layers may be added to the original designed to find solutions that may result in the fabrication of an ICE Core that remains within the target range of the chosen SEC or target design (e.g. within 15%). Each optimization via the 'slack' layer process may begin by removal of any previously added layers and a new investigation of possibly thousands of alternative design choices. The potential design choices are analyzed using the existing fixed layers and predetermined input seeds into the process. Solutions may be discovered and the best solution may be selected and written to the file, the layer number of the resulting filename is indexed, and the file is deposited into the chamber directory.

The system then analyzes the newly deposited file in the process directory based on existing coating results. Optical monitoring wavelengths, constants, tooling factors, turns, next layer thickness, max layer thickness, and initial values are reported. Data is assembled and reported to the fabrication system as an input file indicating instructions for proceeding with the fabrication (step 812). Finally, the system loads the input file to initiate ICE Core fabrication process for layers until completion (step 814).

The previous detailed description is of a small number of embodiments for implementing the claimed inventions and is not intended to limit the scope of the appended claims. For instance, although the ICE Core fabrication system 400 illustrates the use of planetary system type substrate holders, other types of substrate holders may be employed in accordance with the disclosed embodiments. As non-limiting examples, the substrate holders may be a plate or the planets themselves could be the substrate. Similarly, although the ICE Core fabrication system 400 illustrates two thermal sources and two planetary systems, the ICE Core fabrication system 400 may have any number of thermal sources and any number of substrate holders.

In addition, although the disclosed system and method for translating the thermal source and/or the substrate holder is described along with an ion assisted e-beam system (i.e., ICE Core fabrication system 400) and method, the disclosed system and method for translating the thermal source and/or the substrate holder is not limited this particular type of deposition system. For example, the disclosed system and method for translating the thermal source and/or the substrate holder may be applied to other systems such as, but not limited to, reactive magnetron systems, which uses a rotating drum, where the drum holds the substrate that rotates around an axis and a reactive magnetron system (i.e., another type of thermal source) moves relative to the drum. In this type of system, the thermal source may be moved relative to the substrate in similar fashion as described above for improving the uniformity of the ICE Cores. Similarly, the disclosed system and method for translating the thermal source and/or the substrate holder may be applied to atomic layer deposition (ALD) and strong layer deposition processes as well.

In addition to the embodiments described above, many examples of specific combinations are within the scope of the disclosure, some of which are detailed below.

Example 1

A method for manufacturing an integrated computational element (ICE) core, the method including thermally evaporating a material to deposit the material on a substrate, wherein the material is deposited to establish a shape of the ICE core, wherein the shape defines transmission, reflection, and absorptive electromagnetic intensity as a function of wavelength.

Example 2

The method according to Example 1, wherein the ICE core is a multivariate optical element for determining characteristics of liquids, gases, solids, slurries, muds, polymers, multi-phase materials, hydrocarbon fluids, and powders.

Example 3

The method according to Examples 1 or 2, further comprising:
applying a temperature control to the substrate to control a temperature of the substrate.

Example 4

The method according to any of Examples 1-3, further comprising:
controlling at least one characteristic of the material deposited utilizing a performance metric to establish transmission, reflection, and absorption functions of the ICE core.

Example 5

The method according to Example 4, further comprising:
controlling parameters relating to thermal evaporation and deposition to control the transmission, reflection, and absorption functions of the ICE cores.

Example 6

The method according to any of Examples 1-5, wherein the thermal evaporation is performed utilizing an electronic-beam deposition.

Example 7

The method according to any of Examples 1-6, wherein the thermal evaporation is performed utilizing at least one of an electronic-beam deposition, resistive heating, an electromagnetic source, and inductive heating.

Example 8

The method according to any of Examples 1-7, wherein the substrate is subjected to an ion beam source.

Example 9

The method according to any of Examples 1-8, further comprising:
varying e-beam or ion-beam intensities and strengths to control the shape of the ICE core.

Example 10

The method according to any of Examples 1-9, further comprising:
moving the deposition material relative to the substrate during deposition of the material, wherein the movement of the substrate is performed by a single or multi-component planetary mechanism.

Example 11

The method according to any of Examples 1-10, further comprising:
compensating for variations of the conditions and parameters of the first manufacturing system to perform the manufacturing of ICE cores at the one or more other manufacturing systems.

Example 12

The method according to any of Examples 1-11, further comprising:
varying a vacuum level in a chamber encompassing the substrate;
varying background gases in the chamber;
varying a distance between the substrate and a source of the material.

Example 13

The method according to Example 12, wherein the varying of the background gases includes introducing one or more gases.

Example 14

The method according to any of Examples 1-13, further comprising:
masking an evaporation cloud to enhance uniformity of deposition.

Example 15

The method according to any of Examples 1-14, further comprising:
monitoring parameters of the substrate utilizing sensors.

Example 16

The method according to Example 15, wherein the sensor include crystal monitors, optical monitors, in-situ spectrometers, and in-situ ellipsometers.

Example 17

The method according to any of Examples 1-16, further comprising:
evaluating the performance of the ICE core in situ;
adjusting the deposition of the material in response to the performance of the ICE core.

Example 18

The method according to any of Examples 1-17, further comprising:
controlling deposition of a plurality of layers and properties of the plurality of layers, wherein properties of the plurality of layers include at least index of refraction, optical absorption coefficient, physical thickness, and optical thickness.

Example 19

The method according to any of Examples 1-18, wherein a thickness of the ICE core is 20 nm to 50 µm, and wherein a number of layers of the ICE core is 2 to 50.

Example 20

A system for manufacturing ICE cores, the system including: a substrate platen located within a vacuum chamber; and a source of material for deposition on a substrate of the substrate platen to form the ICE cores, wherein the material is deposited to establish a transmission shape of the ICE core.

Example 21

The system according to Example 20, wherein the substrate platen rotates.

Example 22

The system according to Examples 20 or 21, wherein the ICE core is multivariate optical element for determining properties of liquids, gases, slurries, muds, polymers, multiphase materials, hydrocarbon fluids, and powders.

Example 23

The system according to any of Examples 20-22, wherein the evaporation source is heated utilizing an electronic beam that heats the material for deposition on the substrate, and wherein a temperature of the substrate is controlled in real-time

Example 24

The system according to any of Examples 20-23, wherein the evaporation source controls at least one characteristic of the material deposited utilizing a regression vector to establish transmission, reflection and absorption functions of the ICE core.

Example 25

The system according to Example 24, wherein the evaporation source varies intensity and strength of an ion beam focused on the substrate and the electronic beam in real-time to adjust a layer thickness and a refractive index of the ICE core.

Example 26

The system according to any of Examples 20-25, further comprising:
a processing system that utilizes a regression vector between the system and one or more other systems to ensure similar parameters and conditions for manufacturing ICE cores.

Example 27

The system according to Example 26, wherein the processing system adjust the parameters and conditions of the one or more other systems.

Example 28

The system according to Example 26, further comprising:
control logic for varying e-beam and ion-beam intensities and strengths to control the transmission shape of the ICE core.

Example 29

The system according to any of Examples 20-28, wherein the ICE core is utilized to derive information regarding a liquid that is of a greater resolution than a bandwidth utilized by the ICE core.

The following claims set forth a number of the embodiments of the invention disclosed with greater particularity.

The invention claimed is:

1. A method for manufacturing an integrated computational element (ICE) core, the method comprising:
thermally evaporating a material utilizing an electron beam source to deposit the material on a substrate, wherein the material is deposited to establish a shape of the ICE core, wherein the shape defines transmission, reflection, and absorptive electromagnetic intensity as a function of wavelength;
evaluating the performance of the ICE core in situ via an optical monitor assembly;
adjusting the deposition of the material in response to the performance of the ICE core; and
varying an intensity or a strength of an electron beam produced by the electron beam source by varying parameters of the electron beam source to control the shape of the ICE core.

2. The method according to claim 1, further comprising: applying a temperature control to the substrate to control a temperature of the substrate.

3. The method according to claim 1, further comprising: controlling at least one characteristic of the material deposited utilizing a performance metric to establish transmission, reflection, and absorption functions of the ICE core.

4. The method according to claim 1, wherein the substrate is subjected to an ion beam source.

5. The method according to claim 4, further comprising: varying ion-beam intensity or strength to control the shape of the ICE core.

6. The method according to claim 1, further comprising: compensating for variations of the conditions and parameters of the first manufacturing system to perform the manufacturing of ICE cores at the one or more other manufacturing systems.

7. The method according to claim 1, further comprising: varying a vacuum level in a chamber encompassing the substrate; varying background gases in the chamber; varying a distance between the substrate and a source of the material.

8. The method according to claim 1, further comprising: masking an evaporation cloud to enhance uniformity of deposition.

9. The method according to claim 1, further comprising: monitoring parameters of the substrate utilizing sensors, wherein the sensors include crystal monitors, optical monitors, in-situ spectrometers, and in-situ ellipsometers.

10. The method according to claim 1, further comprising: controlling deposition of a plurality of layers and properties of the plurality of layers, wherein properties of the plurality of layers include at least index of refraction, optical absorption coefficient, physical thickness, and optical thickness.

11. A system for manufacturing ICE cores, the system comprising:
a substrate platen located within a vacuum chamber;
a source of material for deposition on a substrate of the substrate platen to form the ICE cores, wherein the material is deposited to establish a transmission shape of the ICE core;
an electronic beam source utilized to heat the material for deposition on the substrate, the electron beam source configured to vary an intensity or a strength of the electron beam in real-time by varying parameters of the electron beam source to adjust a layer thickness and a refractive index of the ICE core; and
an optical monitor assembly configured to evaluate the performance of the ICE core in situ.

12. The system according to claim 11, wherein a temperature of the substrate is controlled in real-time.

13. The system according to claim 11, wherein the source of material for deposition controls at least one characteristic of the material deposited utilizing a regression vector to establish transmission, reflection and absorption functions of the ICE core.

14. The system according to claim 11, further comprising an ion beam source configured to vary an intensity or a strength of an ion beam focused on the substrate in real-time to adjust a layer thickness and a refractive index of the ICE core.

15. The system according to claim 13, further comprising: a processing system that utilizes a regression vector between the system and one or more other systems to ensure similar parameters and conditions for manufacturing ICE cores.

16. The system according to claim 15, wherein the processing system adjust the parameters and conditions of the one or more other systems.

17. The system according to claim 15, further comprising: control logic for varying e-beam and ion-beam intensities and strengths to control the transmission shape of the ICE core.

18. The system according to claim 11, wherein the ICE core is utilized to derive information regarding a liquid that is of a greater resolution than a bandwidth utilized by the ICE core.

* * * * *